US012599760B2

(12) United States Patent
Wasserman et al.

(10) Patent No.: US 12,599,760 B2
(45) Date of Patent: Apr. 14, 2026

(54) ELECTRODE ASSEMBLY HAVING PERFORATED ANISOTROPIC LAYER, AND SYSTEMS AND METHODS OF APPLYING TUMOR-TREATING FIELDS USING SAME

(71) Applicant: NOVOCURE GMBH, Root (CH)

(72) Inventors: Yoram Wasserman, Haifa (IL); Stas Obuchovsky, Haifa (IL); Nataliya Kuplennik, Haifa (IL); David Shapiro, Haifa (IL)

(73) Assignee: NOVOCURE GMBH, Baar (CH)

( * ) Notice: Subject to any disclaimer, the term of this patent is extended or adjusted under 35 U.S.C. 154(b) by 518 days.

(21) Appl. No.: 18/193,937

(22) Filed: Mar. 31, 2023

(65) Prior Publication Data

US 2023/0310336 A1 Oct. 5, 2023

Related U.S. Application Data

(60) Provisional application No. 63/325,948, filed on Mar. 31, 2022.

(51) Int. Cl.
*A61N 1/00* (2006.01)
*A61N 1/04* (2006.01)
*A61N 1/36* (2006.01)

(52) U.S. Cl.
CPC .......... *A61N 1/0492* (2013.01); *A61N 1/0496* (2013.01); *A61N 1/36002* (2017.08)

(58) Field of Classification Search
None
See application file for complete search history.

(56) References Cited

U.S. PATENT DOCUMENTS 8,170,684 B2* 5/2012 Palti .................... A61N 1/0492
607/152
2004/0181264 A1* 9/2004 Silverstone ............ A61N 1/326
607/50

(Continued)

FOREIGN PATENT DOCUMENTS

CN 105 920 731 9/2016
CN 105 969 237 A 9/2016

(Continued)

OTHER PUBLICATIONS

International Search Authority Search Report and Written Opinion for PCT/IB2023/053267, dated Jul. 3, 2023.

*Primary Examiner* — William J Levicky
*Assistant Examiner* — Anant A Gupta
(74) *Attorney, Agent, or Firm* — Ballard Spahr LLP

(57) ABSTRACT

An apparatus includes: at least one electrode element; a layer of anisotropic material; a first layer of conductive adhesive positioned between a skin-facing surface of the at least one electrode element and an outwardly facing surface of the layer of anisotropic material; and a skin contact layer. The skin contact layer includes a biocompatible conductive adhesive and is disposed on a skin-facing side of the layer of anisotropic material. The first layer of conductive adhesive facilitates electrical contact between the skin-facing surface of the at least one electrode element and the outwardly facing surface of the layer of anisotropic material. A plurality of openings extend through the layer of anisotropic material.

20 Claims, 6 Drawing Sheets

(56)     References Cited

U.S. PATENT DOCUMENTS

| | | | |
|---|---|---|---|
| 2006/0195146 A1* | 8/2006 | Tracey .............. | A61N 1/36014 607/3 |
| 2006/0276858 A1 | 12/2006 | Palti | |
| 2013/0197608 A1* | 8/2013 | Eiger ...................... | A61N 1/37 607/2 |
| 2018/0117302 A1 | 5/2018 | Clegg | |
| 2018/0247740 A1* | 8/2018 | Khamphilavong .. | A61B 8/4427 |

FOREIGN PATENT DOCUMENTS

| | | | | |
|---|---|---|---|---|
| KR | 20140145870 A | * 12/2014 | ............. | B32B 9/048 |
| WO | WO 2009/119383 | 10/2009 | | |
| WO | WO 2019/119045 | 6/2019 | | |
| WO | WO-2019119045 A1 | * 6/2019 | .............. | B32B 3/20 |

* cited by examiner

1B'

1B

20

20

30, 40, 50

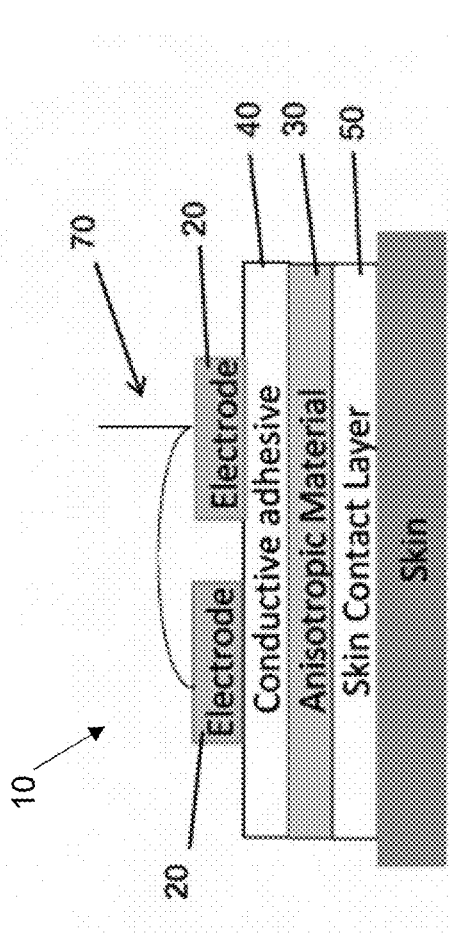
FIG. 1B
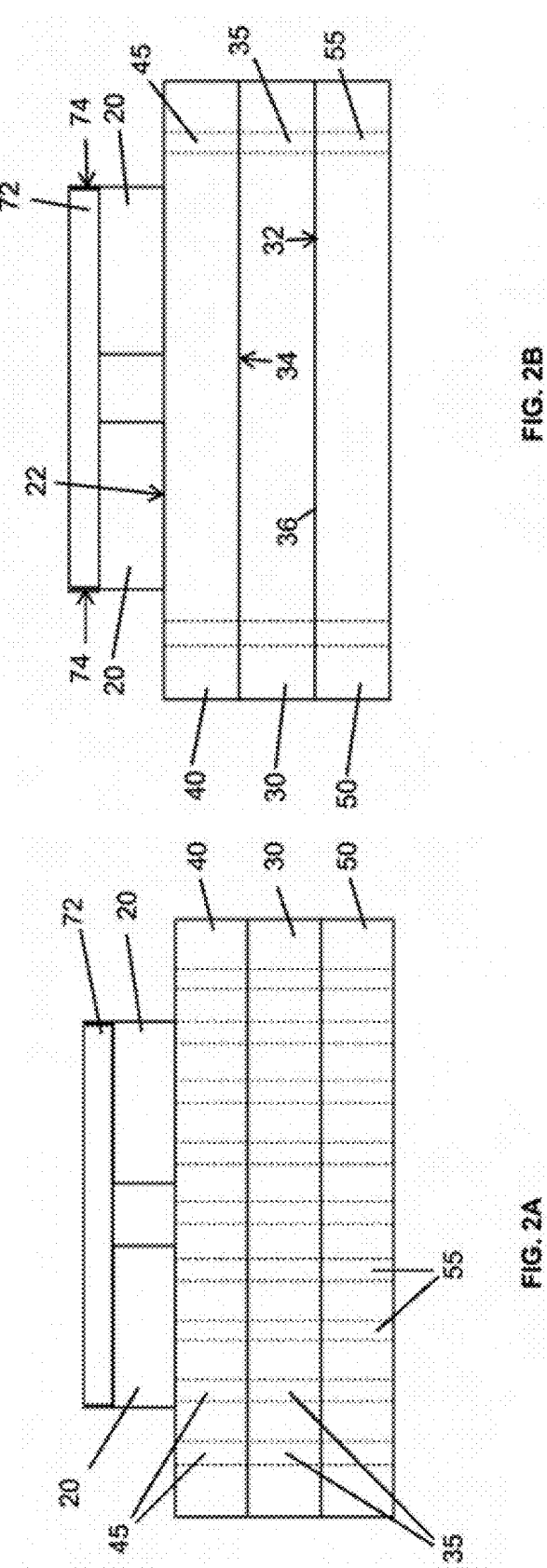
FIG. 2B
FIG. 2A

ELECTRODE ASSEMBLY HAVING PERFORATED ANISOTROPIC LAYER, AND SYSTEMS AND METHODS OF APPLYING TUMOR-TREATING FIELDS USING SAME

CROSS-REFERENCE TO RELATED APPLICATION

This application claims priority to, and the benefit of the filing date of, U.S. Provisional application No. 63/325,948, filed Mar. 31, 2022, the entirety of which is hereby incorporated by reference herein.

BACKGROUND

Tumor Treating Fields (TTFields) therapy is a proven approach for treating tumors using alternating electric fields at frequencies between 50 kHz-1 MHz, such as from 100-500 kHz. The alternating electric fields are induced by electrode assemblies (e.g., arrays of capacitively coupled electrodes, also called transducer arrays) placed on opposite sides of a target location in a subject's body. When an AC voltage is applied between opposing electrode assemblies, an AC current is coupled through the electrode assemblies and into the subject's body. And higher currents are strongly correlated with higher efficacy of treatment.

One potential issue with transducer arrays is the comfort level for the patient. The area of the skin under the electrode can generate heat, and additionally some patients may sweat, both of which can provide at least some level of discomfort for the patient. Additionally, sweat under the array can compromise the contact seal of the electrode element, which in turn may require a higher current to overcome the wasted current loss. Accordingly, a transducer array that is less susceptible to heat and moisture collection and retention against the skin is desirable.

SUMMARY

In various aspects, the disclosure relates to an apparatus having at least one electrode element, a layer of anisotropic material, a first layer of conductive adhesive, and a skin contact layer. The at least one electrode element has a skin-facing surface. The layer of anisotropic material has a skin-facing surface and an opposing outwardly facing surface. The first layer of conductive adhesive is positioned between the skin-facing surface of the at least one electrode element and the outwardly facing surface of the layer of anisotropic material. The skin contact layer includes a biocompatible conductive adhesive and is disposed on a skin-facing side of the layer of anisotropic material. The first layer of conductive adhesive is configured to facilitate electrical contact between the skin-facing surface of the at least one electrode element and the outwardly facing surface of the layer of anisotropic material. A plurality of openings extend through the layer of anisotropic material from the skin-facing surface to the outwardly facing surface.

In other aspects, the disclosure relates to a method that includes forming a plurality of openings that extend through a layer of anisotropic material of an apparatus, wherein the apparatus includes: a first layer of conductive adhesive; a skin contact layer comprising a biocompatible conductive adhesive; and the layer of anisotropic material. The anisotropic material is disposed between the first layer of conductive adhesive and the skin contact layer.

BRIEF DESCRIPTION OF THE DRAWINGS

FIG. 1B is a cross sectional view of the apparatus of FIG. 1A, taken at line 1B-1B'.

FIG. 2A is a close-up cross sectional view of an exemplary apparatus having openings that extend through an anisotropic layer, a conductive adhesive layer, and/or a skin contact layer, as disclosed herein.

FIG. 2B is a close-up cross sectional view of another exemplary apparatus having openings that extend through an anisotropic layer, a conductive adhesive layer, and/or a skin contact layer, as disclosed herein.

Various embodiments are described in detail below with reference to the accompanying drawings, wherein like reference numerals represent like elements.

DETAILED DESCRIPTION

Figure 1A:
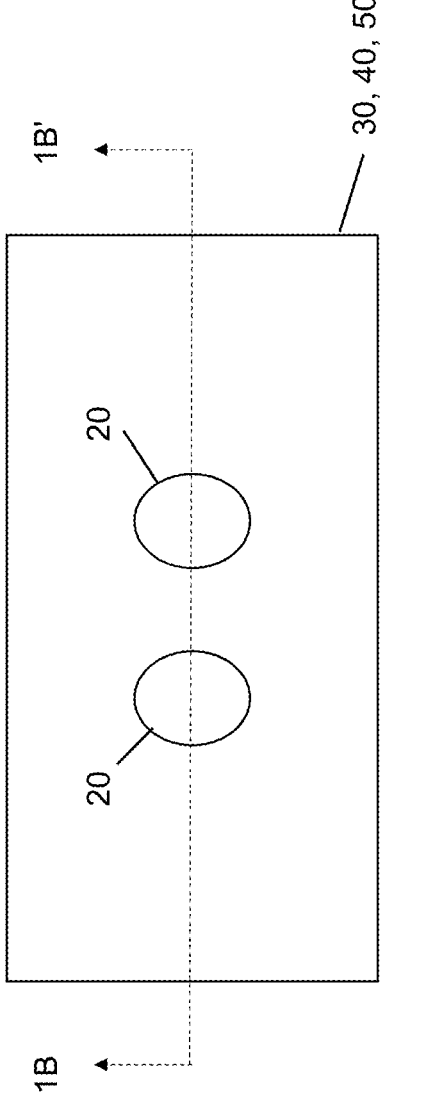
FIG. 1A is a schematic top view of an exemplary apparatus having electrode elements as disclosed herein.

This application describes apparatuses (e.g., exemplary treatment assemblies) that can be used, e.g., for delivering TTFields to a subject's body and treating one or more cancers or tumors located in the subject's body.

The present invention can be understood more readily by reference to the following detailed description, examples, drawings, and claims, and their previous and following description. However, it is to be understood that this invention is not limited to the specific apparatuses, devices, systems, and/or methods disclosed unless otherwise specified, and as such, of course, can vary.

Headings are provided for convenience only and are not to be construed to limit the invention in any manner. Embodiments illustrated under any heading or in any portion of the disclosure may be combined with embodiments illustrated under the same or any other heading or other portion of the disclosure.

Any combination of the elements described herein in all possible variations thereof is encompassed by the invention unless otherwise indicated herein or otherwise clearly contradicted by context.

As used in the specification and the appended claims, the singular forms "a," "an" and "the" include plural referents unless the context clearly dictates otherwise.

Disclosed herein, and with reference to FIGS. 1A-2B, is an apparatus 10 comprising at least one electrode element 20 having a skin-facing surface 22. The apparatus 10 can further comprise a layer of anisotropic material 30 having a skin-facing surface 32 and an opposing outwardly facing surface 34. A first layer of conductive adhesive or conductive gel/hydrogel 40 can be positioned between the skin-facing surface 22 of the at least one electrode element 20 and the outwardly facing surface 34 of the layer of anisotropic material 30. The apparatus 10 can comprise a skin contact layer 50 comprising a biocompatible conductive adhesive or conductive gel/hydrogel. The skin contact layer 50 can be disposed on a skin-facing side 36 of the layer of anisotropic material 30.

The first layer of conductive adhesive or conductive gel/hydrogel 40 can be configured to facilitate electrical contact between the skin-facing surface 22 of the at least one electrode element 20 and the outwardly facing surface 34 of the layer of anisotropic material 30. A plurality of openings 35 (for example, perforations) can extend through the layer of anisotropic material 30 from the skin-facing surface 32 to the outwardly facing surface 34. In this way, moisture can be communicated through the anisotropic material. Further, the openings 35 (e.g., perforations) can provide breathability, thereby allowing heat dissipation. Accordingly, the openings 35 can provide cooling and sweat dissipation. In addition to improving patient comfort, evaporation of the sweat from the outwardly facing surface 34 of the anisotropic material 30 can help avoid any problems from sweat under the electrodes. In some aspects, the plurality of openings (e.g., perforations) may extend through only the layer of aniso-tropic material.

Referring to FIG. 2A, in some aspects, the apparatus 10 can further comprise a second plurality of openings 45 that extend through the first layer of conductive adhesive or conductive gel/hydrogel 40, and/or a third plurality of openings 55 that extend through the skin contact layer 50. The openings of the second plurality of openings 45 or the openings of the third plurality of openings 55, or both, can be coaxially aligned with respective openings of the plurality of openings 35 of the layer of anisotropic material 30. Accordingly, the plurality of openings may extend through only the anisotropic layer; or through more than one layer; or through all layers of the electrode assembly. And, when the openings extend through more than one layer, the openings may, or may not, be coaxially aligned with one or more of the plurality of openings of other layers. In some aspects, the plurality of openings may extend through all of the layers except for the circuit board layer (e.g., optionally, a printed circuit board (PCB) layer). One could construct all of the layers of the electrode assembly and punch a plurality of openings through all of the layers in one action; or one could construct all of the layers except for the circuit board (PCB) layer to form a pre-construct, punch a plurality of openings through all of the layers of the pre-construct in one action, and then add the circuit board (PCB) layer (without openings) to form the electrode assembly.

The cross-sectional area of the openings is not particularly limited. Conveniently, the openings may be of the order of size of a needle or pin prick, but may be significantly smaller, or significantly larger. In a particular electrode assembly construct, the openings may all be of approxi-mately the same size (cross-sectional area), or may vary in size. Furthermore, the dimensions of the cross-sectional area of the openings may be regular in shape (e.g., approximately circular) or irregular (e.g., irregular slit shapes).

Figure 3:
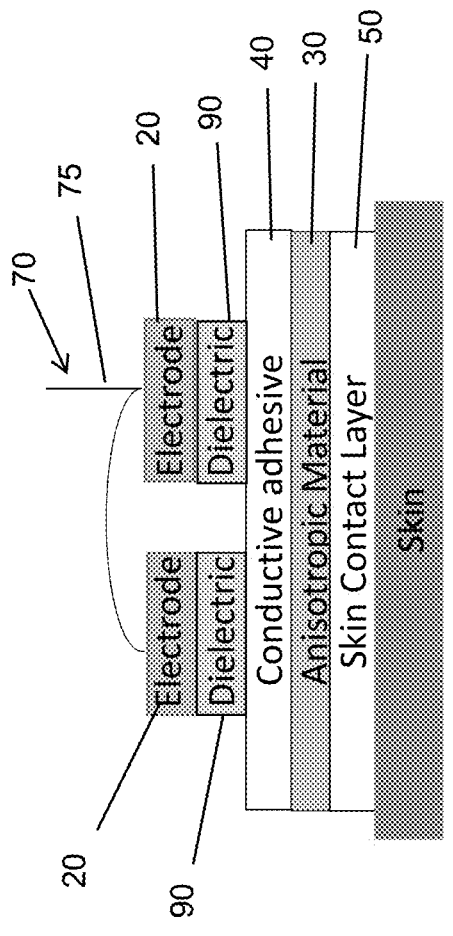
FIG. 3 is a cross sectional representation of an exemplary apparatus having dielectric elements that are coupled to respective electrode elements as disclosed herein.

Referring to FIGS. 1B, 2B, 3, and 4, the apparatus 10 can comprise an electrical connection 70. For example, in some aspects, the apparatus 10 can comprise a circuit board 72 (e.g., optionally, a printed circuit board (PCB)). In some aspects, the at least one electrode 20 can be coupled to the circuit board 72. In further aspects, the at least one electrode 20 can be a component of the circuit board 72. In still further aspects, and as illustrated in FIG. 3, the electrical connection 70 can comprise a wire 75.

Figure 5A:
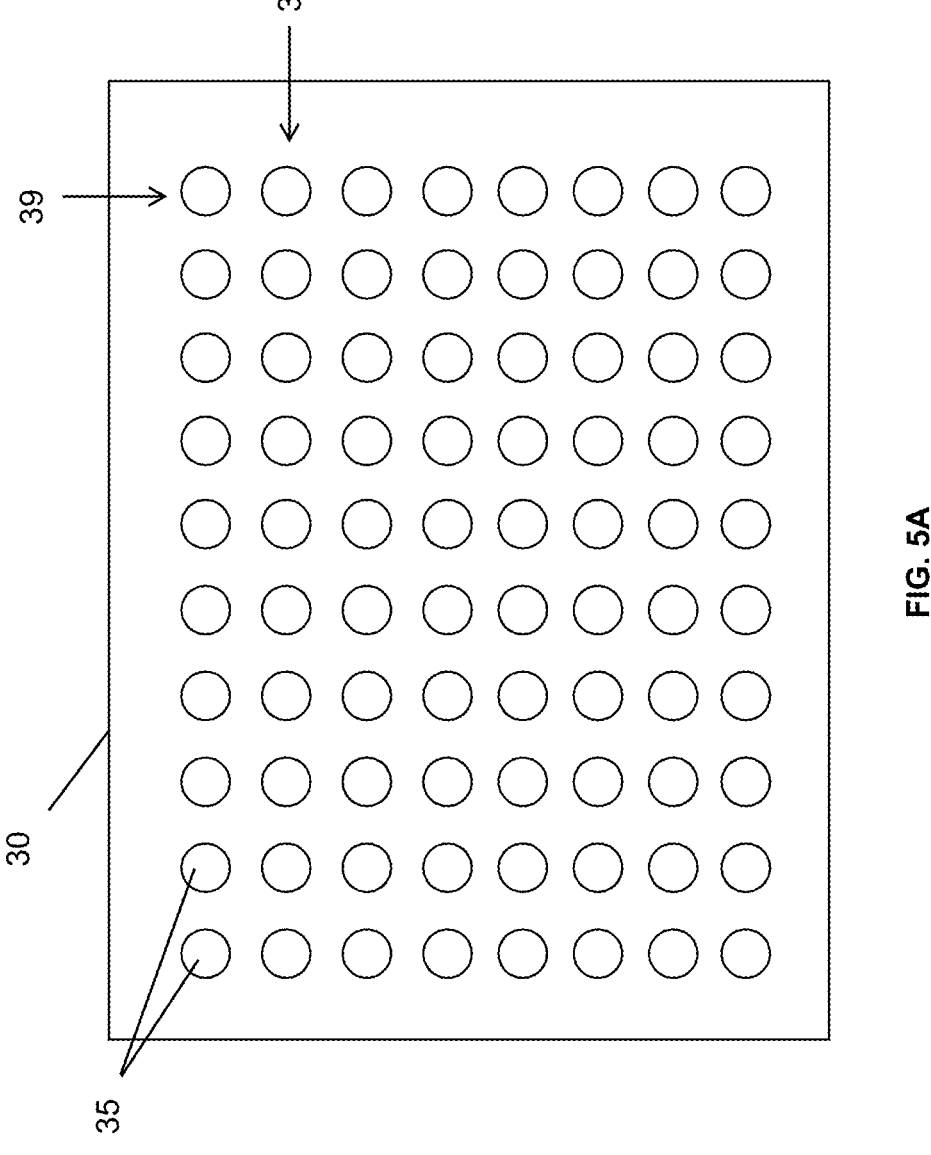
FIG. 5A is a schematic top view of an exemplary anisotropic layer having a plurality of openings as disclosed herein.
Figure 5B:
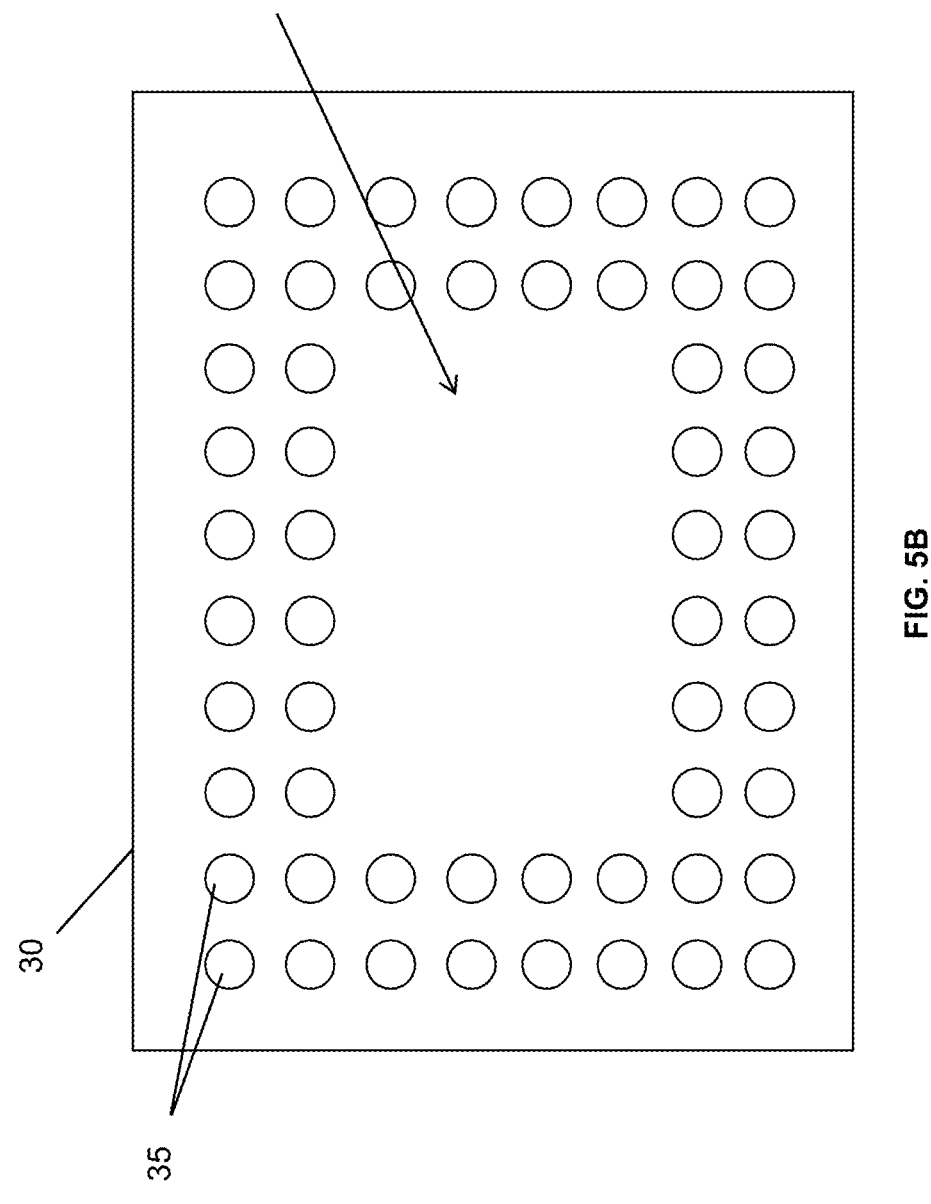
FIG. 5B is a schematic top view of another exemplary anisotropic layer having a plurality of openings as disclosed herein.

Referring to FIG. 2B, the circuit board 72 can have an outer perimeter 74. The outer perimeter can have an outer perimeter shape. The outer perimeter shape can be superimposable on the layer of anisotropic material 30. In some aspects, and as shown in FIG. 2B, all of the plurality of openings 35 through the layer of anisotropic material 30 can be positioned outside of the outer perimeter shape. Accord-ingly, in some aspects, and with further reference to FIG. 5B, the layer of anisotropic material 30 can comprise an interior region with no openings 38. In some aspects, the interior region with no openings 38 can be partially or entirely surrounded by an area with openings 35. In some aspects, and with reference to FIG. 2A, at least one opening of the plurality of openings 35 through the layer of anisotropic material 30 can be positioned within the outer perimeter shape superimposed on the layer of anisotropic material 30. In some aspects, and as illustrated in FIG. 2B, at least one electrode 20 (optionally, all of the electrodes) can be posi-tioned within the outer perimeter 74 of the circuit board 72.

Referring to FIG. 3, in some optional aspects, the appa-ratus 10 can comprise at least one dielectric element 90. A respective dielectric element 90 can be coupled to each electrode element of the at least one electrode element 20. In further aspects and as illustrated in FIG. 1B, the dielectric element(s) 90 can be omitted.

Figure 4:
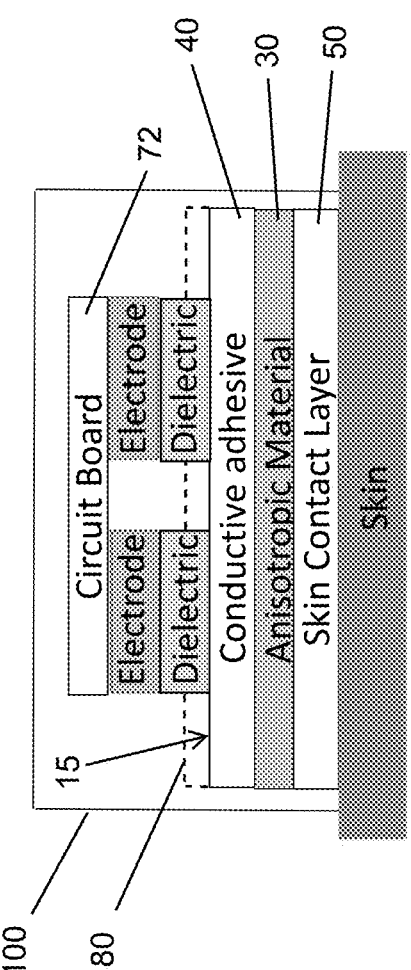
FIG. 4 is a cross sectional representation of an exemplary apparatus having an absorbent or wicking material that overlies an outwardly facing surface of the apparatus, as disclosed herein.

In some optional aspects, and as illustrated in FIG. 4, the apparatus 10 can comprise an absorbent or wicking material 80 that overlies at least a portion of (optionally, an entirety of) an outwardly facing surface 15 of the apparatus. Option-ally, the absorbent or wicking material 80 can comprise a woven material or a superabsorbent material. For example, the superabsorbent material can comprise cross-linked poly acrylic acid and/or copolymers thereof.

In various aspects, a cover 100 can extend over the apparatus 10. For example, in some aspects, the cover 100 and skin of the patient can cooperate to enclose the apparatus 10. For example, the cover 100 may be a breathable overlay bandage or plaster.

In some aspects, the first layer of conductive adhesive or conductive gel/hydrogel 40 can comprise a dielectric mate-rial and conductive particles dispersed within the dielectric material. In some aspects, at least a portion of the conductive particles can define a conductive pathway through a thick-ness of the first layer of conductive adhesive or conductive gel/hydrogel 40.

In some optional aspects, the layer of anisotropic material 30 can comprise graphite. In various aspects, the layer of anisotropic material 30 can comprise pyrolytic graphite, graphitized polymer, or graphite foil made from compressed high purity exfoliated mineral graphite.

The arrangement of the plurality of openings 35 can be regular or irregular. For example, referring to FIG. 5, in some optional aspects, the plurality of openings 35 through the layer of anisotropic material 30 can be arranged in rows 37 and columns 39. In other aspects, the plurality of open-ings may be arranged in an entirely random fashion. Adja-cent openings of the plurality of openings 35 can have consistent spacing or different spacing. The number of openings and the size of openings can be selected based on desired properties. For example, more openings and larger openings can improve breathability, but too many openings, or too large of an area defined by openings, can reduce the conductivity properties of the layer of anisotropic material. In exemplary aspects, the size of the openings (e.g., perfo-rations) can have a cross-sectional dimension (e.g., diam-eter) from about 0.1 mm to about 0.2 mm, such as, for example, from about 0.2 mm to about 2 mm.

Optionally, the apparatus 10 can comprise a plurality of electrode elements 20. In other aspects, the apparatus 10 can have only a single electrode 20.

5

Figure 6:
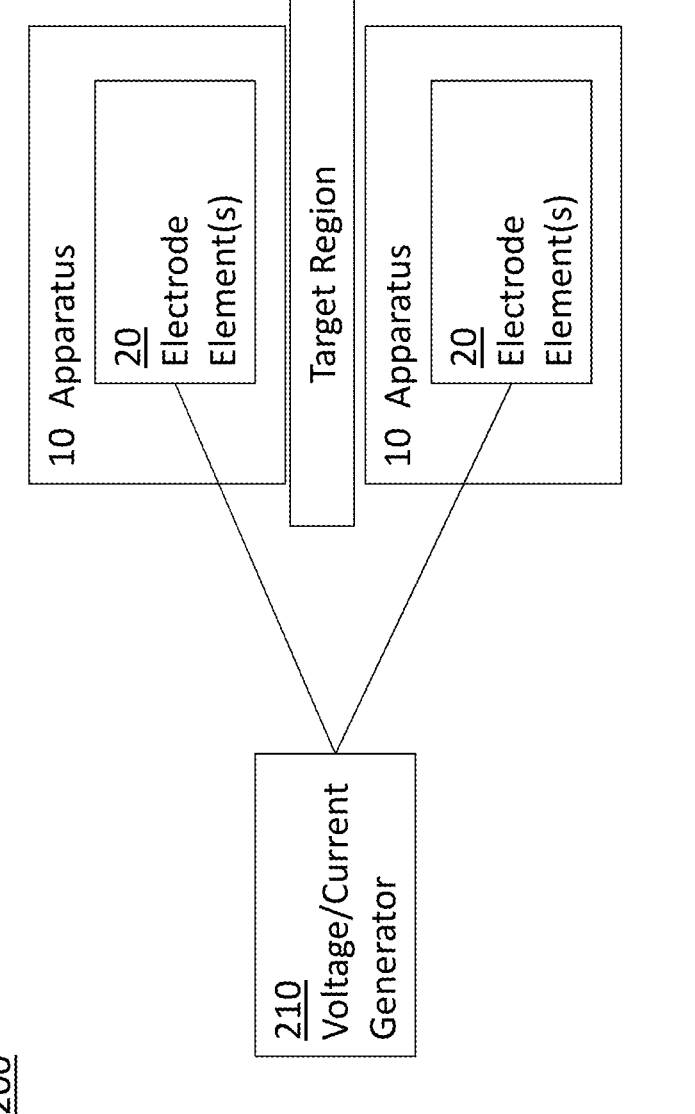
FIG. 6 is a block diagram showing an exemplary system for delivering TTFields to a target region of a patient using an apparatus as disclosed herein.

A method of using an apparatus 10 as disclosed herein can comprise applying an electrical field using the at least one electrode element 20 of the apparatus. FIG. 6 illustrates an exemplary system 200 for applying electrical fields using apparatuses 10 as disclosed herein. A plurality of apparatuses 10 (e.g., two apparatuses, as illustrated) can be positioned with a target region therebetween. A voltage or current generator 210 can be in communication with the at least one electrode 20 of each apparatus 10. The voltage or current generator 210 can be configured to generate electric fields through the target region.

The method can include positioning a first of the apparatuses 10 at a first position on or in the subject's body. For example, the apparatus 10 can be positioned on the subject's skin at the right of the subject's head facing a target region (e.g., a tumor in the brain.)

A second of the apparatuses 10 can be positioned at a second position on or in the patient's body. For example, the second apparatus 10 can be positioned on the subject's skin at the left of the patient's head facing the target region.

An alternating voltage can be applied between the apparatuses 10. The applying may be implemented by applying the alternating voltage between (i) a first electrode element disposed in electrical contact with the layer of anisotropic material 30 of the first apparatus 10 and (ii) a second electrode element disposed in electrical contact with the layer of anisotropic material 30 of the second apparatus 10.

In some embodiments, the frequency of the alternating voltage is between 50 kHz and 1 MHz, or between 100 kHz and 500 kHz. In some aspects, the AC voltage generator can be controlled by a controller. The controller can use temperature measurements to control the amplitude of the current to be delivered via the apparatuses 10 in order to maintain temperatures below a safety threshold (e.g., 41° C.). This can be accomplished, for example, by measuring a first temperature of the first electrode element, measuring a second temperature of the second electrode element, and controlling the applying of the alternating voltage based on the first temperature and the second temperature, as described below.

More specifically, temperature sensors (e.g., thermistors) can be positioned in thermal contact with respective electrode elements within each of the apparatuses 10. The temperature sensors can measure respective first and second temperatures (e.g., at first and second electrode elements in the first and second apparatuses 10, respectively), and the controller can control the output of the AC voltage generator based on these temperatures.

A method of making an apparatus as disclosed herein can comprise forming a plurality of openings 35 that extend through the layer of anisotropic material 30 of the apparatus 10, the apparatus comprising: a first layer of conductive adhesive or conductive gel/hydrogel 40, a skin contact layer 50 comprising a biocompatible conductive adhesive or conductive gel/hydrogel, and the layer of anisotropic material, wherein the anisotropic material is disposed between the first layer of conductive adhesive or conductive gel/hydrogel 40 and the skin contact layer 50.

In some optional aspects, the second plurality of openings 45 that extend through the first layer of conductive adhesive or conductive gel/hydrogel 40 can be formed, and the third plurality of openings 55 that extend through the skin contact layer 50 can be formed. The openings of the second plurality of openings 45 and the openings of the third plurality of openings 55 can be coaxially aligned with respective openings of the plurality of openings 35 that extend through the layer of anisotropic material 30. In exemplary aspects, the pluralities of openings 35, 45, and 55 can be formed together. That is, the openings can be formed through an assembly comprising the layer of anisotropic material 30, first layer of conductive adhesive or conductive gel/hydrogel 40, and the skin contact layer 50.

In some aspects, the apparatus 10 can comprise a circuit board 72 that is coupled to the first layer of conductive adhesive, the circuit board having an outer perimeter. The first layer of conductive adhesive 40 can be disposed between the circuit board 72 and the layer of anisotropic material 30. In some aspects, the plurality of openings 35 in the layer of anisotropic material 30 can be formed only outside of the perimeter of the circuit board 72.

In further aspects, the circuit board 72 can be coupled to the first layer of conductive adhesive 40 after forming the plurality of openings 35 in the layer of anisotropic material 30.

In some aspects, the plurality of openings 35 can be formed with a roller having protrusions (for example, needles) configured to provide such openings/perforations. In further aspects, the plurality of openings 35 can be formed by a press having protrusions configured to provide such openings, or by a stamping machine.

Optionally, portions of the layer of anisotropic material 30 can be removed to form the plurality of openings 35 in the layer of anisotropic material 30. For example, the layer of anisotropic material 30 can be punched to form the plurality of openings 35. In further aspects, the layer of anisotropic material 30 can be pierced to form the openings 35.

In an example, Moisture Vapor Transmission Rate (MVTR) was measured for four different material samples, each having a different number of openings through the layer of anisotropic material. Each material sample (layered construct) comprised a skin contact layer comprising carbon filled pressure sensitive adhesive, a layer of anisotropic material comprising pyrolytic graphite, and a first layer of conductive adhesive comprising carbon filled pressure sensitive adhesive. In the example, 15 milliliters of distilled water was placed in plastic petri dish (D=5.5 cm) and tightly sealed with tested apparatuses. Petri dishes were then placed on a heating plate (37° C.), at room temperature. After 24 hours, weight of the water vapor transmitted through the layered construct was measured by differential weighting. Table 1 illustrates the effect of the openings on the MVTR:

TABLE 1

| Hole amount | MVTR (g/m2/24 h) |
|---|---|
| No holes | 519 |
| 39 | 660 |
| 78 | 1400 |
| 117 | 1400 |

Accordingly, the openings 35 (e.g., perforations) in the layer of anisotropic material allow moisture to escape from under the layered construct.

When TTFields are applied to a subject's body, the temperature at the subject's body may increase proportionally to the induced electric field. Regulations limit the amount of current that can be driven through a transducer array to an amount that keeps the measured temperature at locations on the subject's body below a temperature threshold. As practiced in the art, the temperature at the location of the transducer arrays on the subject's body is controlled to be below the temperature threshold by reducing the operational current driven by the transducer arrays and reducing the strength of the resulting TTFields. This in turn becomes an over-riding limitation on the TTFields strength that can be used to treat the tumor.

An uneven distribution of current through the transducer array due to either the distribution of the electrode elements or the edge effect can lead to higher temperature zones (or "hot spots") e.g., at the corners or edges of the transducer array. These hot spots are the locations that reach the threshold temperature first and therefore control the requirement to reduce the current. As such, the generation of hot spots limits the maximum operational current that may be driven by a transducer array, and the strength of the resulting TTFields.

The inventors have now recognized that a need exists for transducer arrays that reduce or minimize uneven distribution of current and thereby allow the application of higher operating currents. Transducer arrays operated with increased current can induce stronger TTFields in the subject's body, ultimately leading to better patient outcomes. The apparatuses (e.g. electrode assemblies) disclosed herein allow current and heat to be spread evenly over the array thereby minimizing or eliminating hot spots.

Advantageously, in addition to facilitating the removal of sweat and moisture from under the electrodes, the breathability of the apparatus 10, via the plurality of openings 35, can further reduce the temperature at the body. Accordingly, the disclosed apparatus can increase the potential TTFields strength that can be applied.

The embodiments described herein incorporate into the electrode assembly a sheet of material having anisotropic thermal properties and/or anisotropic electrical properties (referred to herein also as the layer of anisotropic material 30). If the sheet of material has anisotropic thermal properties (e.g., greater in-plane thermal conductivity than perpendicular to the plane), then the sheet spreads the heat out more evenly over a larger surface area. If the sheet of material has anisotropic electrical properties (e.g., greater in-plane electrical conductivity than perpendicular to the plane; or, conversely, lower in-plane resistance than perpendicular to the plane), then the sheet spreads the current out more evenly over a larger surface area. In each case, this lowers the temperature of the hot spots and raises the temperature of the cooler regions when a given AC voltage is applied to the electrode assembly (as compared to the prior art configuration described above). Accordingly, the current can be increased (thereby increasing the therapeutic effect) without exceeding the safety temperature threshold at any point on the subject's skin.

In some embodiments, the anisotropic material is anisotropic with respect to electrical conductivity properties. In some embodiments, the anisotropic material is anisotropic with respect to thermal conductivity properties. In some embodiments, the anisotropic material is anisotropic with respect to both electrical conductivity properties and thermal conductivity properties.

The anisotropic thermal properties include directional thermal properties. Specifically, the sheet has a first thermal conductivity in a direction that is perpendicular to its front face. And the thermal conductivity of the sheet in directions parallel to the front face is more than two times higher than the first thermal conductivity. In some preferred embodiments, the thermal conductivity in the parallel directions (in the plane of the sheet) is more than ten times higher than the first thermal conductivity. For example, the thermal conductivity of the sheet in directions that are parallel to the front face may be more than: 1.5 times, 2 times, 3 times, 5 times, 10 times, 20 times, 100 times, 200 times, or even more than 1,000 times higher than the first resistance.

The anisotropic electrical properties include directional electrical properties. Specifically, the sheet has a first resistance in a direction that is perpendicular to its front face. And resistance of the sheet in directions parallel to the front face is less than the first resistance. In some preferred embodiments, the resistance in the parallel directions is less than half of the first resistance or less than 10% of the first resistance. For example, the resistance of the sheet 70 in directions that are parallel to the front face may be less than: 75%, 50%, 40%, 30%, 20%, 10%, 5%, 1%, 0.5%, or even less than 0.1% of the first resistance.

In some embodiments (e.g., when the sheet of anisotropic material is a sheet of pyrolytic graphite), the sheet of anisotropic material has both anisotropic electrical properties and anisotropic thermal properties.

In some embodiments (e.g., when the sheet of anisotropic material is a sheet of pyrolytic graphite), the sheet of anisotropic material is nonmetallic. These embodiments are particularly advantageous in situations where preventing the transfer of ions into a subject's body is desirable. More specifically, using a metallic sheet could result in the transfer of ions into a subject's body. In situations where this is not desirable, embodiments that use nonmetallic sheets of anisotropic material are preferable.

FIG. 1A is a schematic representation of an electrode assembly 10 of an embodiment including electrode elements used for applying TTFields to a subject's body. In FIG. 1A, only two electrode elements 20 are shown, but additional electrode elements may be included in the apparatus 10. In alternative embodiments, the apparatus 10 includes only a single electrode element 20. Notably, FIG. 1A depicts an apparatus 10 generically, and the apparatus can have different configurations (e.g., as described below in connection with FIGS. 1B-4).

FIG. 1B is a cross sectional representation of a first embodiment of an electrode assembly 10 including electrode elements 20, taken along the dashed line 1B-1B', in FIG. 1A.

In the FIG. 1B embodiment, the apparatus 10 includes a layer of anisotropic material 30. This layer of anisotropic material 30 has a first thermal conductivity in a direction that is perpendicular to the front face. Thermal conductivity of the layer of anisotropic material 30 in directions that are parallel to the front face is more than two times higher than the first thermal conductivity. In some embodiments, the thermal conductivity of the layer of anisotropic material 30 in directions that are parallel to the front face is more than ten times higher than the first thermal conductivity. The layer of anisotropic material 30 in the FIG. 1B embodiment can also be anisotropic in another respect. More specifically, the layer of anisotropic material 30 can have a first resistance in a direction that is perpendicular to the front face, and the resistance of the sheet in directions that are parallel to the front face can be less than half of the first resistance. In some embodiments, the resistance of the sheet in directions that are parallel to the front face is less than 10% of the first resistance.

In some embodiments, the layer of anisotropic material 30 is a sheet of pyrolytic graphite. Thermal conductivity of pyrolytic graphite sheets in directions that are parallel to the front face of those sheets (i.e., in the a-b plane) is typically more than 50 times higher than the thermal conductivity of those sheets in directions that are perpendicular to the front face (i.e., in the c direction). And electrical resistivity of pyrolytic graphite sheets in directions that are parallel to the front face of those sheets (i.e., in the a-b plane) is typically less than 2% of the electrical resistivity of those sheets in directions that are perpendicular to the front face (i.e., in the c direction).

In other embodiments, the layer of anisotropic material 30 is a graphitized polymer film, such as graphitized polyimide. In other embodiments, the layer of anisotropic material 30 is graphite foil made from compressed high purity exfoliated mineral graphite. In other embodiments, the anisotropic material may be pyrolytic carbon. Other embodiments may utilize sheets of other conducting materials with anisotropic properties. In some embodiments (e.g., when the sheet of anisotropic material is a sheet of pyrolytic graphite), the layer of anisotropic material 30 is nonmetallic.

The electrode assembly 10 in FIG. 1B further includes a skin contact layer 50 of biocompatible conductive material disposed on the skin facing surface of the layer of anisotropic material 30. The skin contact layer 50 is configured to ensure good electrical contact between the device and the body. In some embodiments, the skin contact layer 50 can cover the entire front face of the layer of anisotropic material 30. The skin contact layer 50 can be the same size or larger than the layer of anisotropic material 30. In some embodiments, the skin contact layer 50 comprises hydrogel. In these embodiments, the hydrogel may have a thickness between 50 and 2000 μm. In other embodiments, the skin contact layer 50 comprises a conductive adhesive composite as further disclosed herein.

In the embodiments shown in FIGS. 3 and 4, the dielectric material 90 (e.g., ceramic) can be positioned against the skin facing surface 22 of each electrode element 20.

In some embodiments, the layer of anisotropic material 30 has a centroid, and the centroid of the skin facing surface 22 of at least one electrode element 20 can be positioned less than 3 cm away from the centroid of the layer of anisotropic material 30. In some embodiments, the layer of anisotropic material 30 has a centroid and a dimension parallel to the rear face of the layer of anisotropic material 30 (e.g., a length or a width), and the centroid of the first front face of the electrode element 20 is positioned away from the centroid of the layer of anisotropic material 30 by less than 10% of the dimension.

The electrode elements 20 can comprise metal. The electrode elements 20 can be wired together (e.g., using wires, traces on a flex circuit, etc.) to a lead. The wire 75 (FIG. 3) can supply an AC voltage from the voltage/current generator 210 (FIG. 6) to the electrode elements to generate the TTFields when the apparatus 10 is affixed to the subject's body for treatment.

In some aspects, in which the at least one electrode comprises a plurality of electrodes, the area of the layer of anisotropic material 30 is larger (e.g., at least 10 times larger) than the combined areas of the plurality of electrode elements 20. When an AC voltage is applied to the electrode elements 20, heat spreads out across the entire layer of anisotropic material 30, which minimizes or eliminates hot spots.

Apparatuses Having Layers that Comprise a Conductive Adhesive Composite

Optionally, the conductive adhesive layer 40 and/or the skin contact layer 50 can be or can comprise hydrogel. It is further contemplated that the conductive adhesive layer 40 and/or the skin contact layer 50 can be or can comprise conductive adhesive composites (described further below) rather than hydrogel.

In exemplary aspects, the conductive adhesive composite can comprise a dielectric material and conductive particles dispersed within the dielectric material. In some aspects, at least a portion of the conductive particles define a conductive pathway through a thickness of the conductive adhesive composite. In some aspects, it is contemplated that the conductive particles can be aligned in response to application of an electric field such that the conductive particles undergo electrophoresis. In some aspects, the dielectric material is a polymeric adhesive. Optionally, in these aspects, the polymeric adhesive can be an acrylic adhesive. In some aspects, the conductive particles can comprise carbon. Optionally, in these aspects, the conductive particles can comprise graphite powder. Additionally, or alternatively, the conductive particles can comprise carbon flakes. Additionally, or alternatively, the conductive particles can comprise carbon granules. Additionally, or alternatively, the conductive particles can comprise carbon nanotubes. Additionally, or alternatively, the conductive particles can comprise carbon black powder. In further aspects, the conductive adhesive composite further comprises a polar material (e.g., a polar salt). The polar salt may be a quaternary ammonium salt, such as a tetra alkyl ammonium salt. Exemplary conductive adhesive composites, as well as methods for making such conductive adhesive composites, are disclosed in U.S. Pat. Nos. 8,673,184 and 9,947,432, which are incorporated herein by reference for all purposes. In exemplary aspects, the conductive adhesive composite can be a dry carbon/salt adhesive, such as the OMNI-WAVE adhesive compositions manufactured and sold by FLEXCON (Spencer, MA, USA); or ARcare® 8006 electrically conductive adhesive composition manufactured and sold by Adhesives Research, Inc. (Glen Rock, PA, USA).

In exemplary aspects, the skin contact layer 50 does not comprise hydrogel.

In further exemplary aspects, the skin contact layer 50 does not comprise a latex rubber polymer.

In further exemplary aspects, the skin contact layer of the electrode assemblies does not comprise silver or silver chloride.

In still further aspects, the conductive adhesive composite layer has a thickness ranging from about 30 μm to about 2000 μm, such as from 30 μm to about 70 μm. Optionally, the conductive adhesive composite can have a thickness ranging from about 45 μm to about 55 μm In still further aspects, the conductive adhesive composite does not comprise water.

In exemplary aspects, the conductive particles of the conductive adhesive composite comprise a plurality of groups of conductive particles. In these aspects, the conductive particles of the combined groups of conductive particles may be aligned to define a respective conductive pathway through the thickness of the conductive in the adhesive composite electrode assemblies.

In further exemplary aspects, and as disclosed above, an apparatus can comprise: at least one electrode element having a skin-facing surface; a layer of anisotropic material having a skin-facing surface and an opposing outwardly facing surface; and a skin contact layer comprising a conductive adhesive composite or conductive gel/hydrogel. In these aspects, the at least one electrode element can be electrically coupled to (optionally, in electrical contact with) the outwardly facing surface of the layer of anisotropic material, and the skin contact layer can be disposed on the skin-facing surface of the layer of anisotropic material.

Optionally, in exemplary aspects, the skin contact layer can be releasably connected to the layer of anisotropic material. In these aspects, it is contemplated that the skin contact layer can be selectively detached from the anisotropic material and replaced with a new skin contact layer (for example, when a maximum/threshold duration of use is approached or met).

In exemplary aspects, the sheet of anisotropic material is a sheet of synthetic graphite.

In exemplary aspects, the sheet of anisotropic material is a sheet of pyrolytic graphite, or a sheet of graphitized polymer, such as graphitized polyimide.

In exemplary aspects, the sheet of anisotropic material is graphite foil made from compressed high purity exfoliated mineral graphite.

In exemplary aspects, the sheet of anisotropic material is nonmetallic.

In exemplary aspects, the sheet of anisotropic material has a first thermal conductivity in a direction that is perpendicular to the plane of the sheet, and thermal conductivity of the sheet in directions that are parallel to the plane of the sheet is more than two times higher than the first thermal conductivity.

In exemplary aspects, the sheet of anisotropic material has a first resistance in a direction that is perpendicular to the plane of the sheet, and wherein resistance of the sheet in directions that are parallel to the plane of the sheet is less than half the first resistance. Optionally, in exemplary aspects, the apparatus can further comprise a release liner that covers the skin contact layer. In these aspects, it is contemplated that, prior to use, the apparatus can be provided with the release liner to ensure that the skin contact layer does not adhere to undesirable surfaces or locations. Immediately prior to use, the release liner can be removed, and the skin contact layer can be positioned in contact with the skin of the patient.

In exemplary aspects, by using a conductive adhesive composite as a skin contact layer as disclosed herein, it is contemplated that additional backing and/or cover layers (such as, for example self-adhesive backing or overlay bandage) can be omitted. In these aspects, it is contemplated that the conductive adhesive composite can provide sufficient adhesion to the skin such that it is unnecessary to provide additional layers to maintain a desired position of the electrode assembly on the body of the subject, thereby improving ease of use and decreasing the overall cost of manufacture and use.

In further aspects, by avoiding the use of hydrogel within an electrode assembly, it is contemplated that electrode assemblies comprising conductive adhesive composites as disclosed herein do not require moisture barrier packaging, thereby making the cost of packaging far more affordable. Additionally, it is contemplated that the conductive adhesive composites of the disclosed electrode assemblies can avoid the signal variation issues of hydrogels, thereby providing consistent material properties (e.g., tackiness) and reliable performance during delivery of TTFields. Further, it is contemplated that the disclosed conductive adhesive composites can have a far greater shelf life than hydrogels, thereby decreasing the frequency at which electrode assemblies (or the skin contact layers of electrode assemblies) must be replaced.

It is further contemplated that embodiments that include the sheet of anisotropic material may additionally aid in avoiding or reducing overheating of the electrodes and associated discomfort on the skin by dissipating both electrical current and heat in a lateral (in-plane) direction rather than passing directly through the layer (in a direction perpendicular to the plane of the skin contact layer) in a concentrated manner.

Exemplary Aspects

In view of the described products, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: An apparatus comprising:

at least one electrode element having a skin-facing surface;

a layer of anisotropic material having a skin-facing surface and an opposing outwardly facing surface;

a first layer of conductive adhesive positioned between the skin-facing surface of the at least one electrode element and the outwardly facing surface of the layer of anisotropic material; and a skin contact layer comprising a biocompatible conductive adhesive, wherein the skin contact layer is disposed on a skin-facing side of the layer of anisotropic material, wherein the first layer of conductive adhesive is configured to facilitate electrical contact between the skin-facing surface of the at least one electrode element and the outwardly facing surface of the layer of anisotropic material, wherein a plurality of openings extend through the layer of anisotropic material from the skin-facing surface to the outwardly facing surface.

Aspect 2: The apparatus of aspect 1, further comprising a second plurality of openings that extend through the first layer of conductive adhesive, and a third plurality of openings that extend through the skin contact layer, wherein the openings of the second plurality of openings and the openings of the third plurality of openings are coaxially aligned with respective openings of the plurality of openings of the layer of anisotropic material.

Aspect 3: The apparatus of aspect 1 or aspect 2, further comprising a circuit board, wherein the at least one electrode is coupled to or a component of the circuit board.

Aspect 4: The apparatus of aspect 3, wherein the circuit board has an outer perimeter, having an outer perimeter shape, the outer perimeter shape is superimposable on the layer of anisotropic material, and wherein all of the plurality of openings through the layer of anisotropic material are positioned outside of the outer perimeter shape.

Aspect 5: The apparatus of aspect 3, wherein the circuit board has an outer perimeter, wherein at least one electrode of the at least one electrode is positioned within the outer perimeter of the circuit board.

Aspect 6. The apparatus of aspect 2, wherein all of the plurality of openings extend through all layers of the apparatus except the circuit board.

Aspect 7: The apparatus of any one of the preceding aspects, further comprising an absorbent or wicking material that overlies at least a portion of an outwardly facing surface of the apparatus.

Aspect 8: The apparatus of aspect 7, wherein the absorbent or wicking material comprises a woven material or a superabsorbent material.

Aspect 9: The apparatus of aspect 8, wherein the superabsorbent material comprises cross-linked poly acrylic acid and/or copolymers thereof.

Aspect 10: The apparatus of any one of the preceding aspects, further comprising at least one dielectric element, wherein a respective dielectric element of the at least one dielectric element is coupled to each electrode element of the at least one electrode element.

Aspect 11: The apparatus of any one of the preceding aspects, wherein the first layer of conductive adhesive comprises:

a dielectric material; and conductive particles dispersed within the dielectric material. In an embodiment, at least a portion of the conductive particles define a conductive pathway through a thickness of the first layer of conductive adhesive.

Aspect 12: The apparatus of any one of the preceding aspects, wherein the anisotropic material comprises graphite.

Aspect 13: The apparatus of any one of the preceding aspects, wherein the anisotropic material comprises pyrolytic graphite, graphitized polymer, or graphite foil made from compressed high purity exfoliated mineral graphite.

Aspect 14: A method comprising:

applying an electrical field using the at least one electrode element of the apparatus of any one of the preceding aspects.

Aspect 15: A method comprising:

forming a plurality of openings that extend through a layer of anisotropic material of an apparatus, the apparatus comprising:

a first layer of conductive adhesive;

a skin contact layer comprising a biocompatible conductive adhesive; and the layer of anisotropic material, wherein the anisotropic material is disposed between the first layer of conductive adhesive and the skin contact layer.

Aspect 16: The method of aspect 15, further comprising forming a second plurality of openings that extend through the first layer of conductive adhesive, and a third plurality of openings that extend through the skin contact layer, wherein the openings of the second plurality of openings and the openings of the third plurality of openings are coaxially aligned with respective openings of the plurality of openings that extend through the layer of anisotropic material.

Aspect 17: The method of aspect 15, wherein the apparatus comprises a circuit board that is coupled to the first layer of conductive adhesive, wherein the circuit board has an outer perimeter, wherein the first layer of conductive adhesive is disposed between the circuit board and the layer of anisotropic material, and wherein forming the plurality of openings in the layer of anisotropic material comprises forming the plurality of openings only outside of the perimeter of the circuit board.

Aspect 18: The method of aspect 15, further comprising coupling a circuit board to the first layer of conductive adhesive after forming the plurality of openings in the layer of anisotropic material.

Aspect 19: The method of any one of aspects 15-18, wherein forming the plurality of openings in the layer of anisotropic material comprises forming the plurality of openings with a roller having protrusions configured to provide such openings.

Aspect 20: The method of any one of aspects 17-19, wherein forming the plurality of openings in the layer of anisotropic material comprises removing portions of the layer of anisotropic material to form the plurality of openings.

Aspect 21: The method of any one of aspects 15-20, wherein the layer of anisotropic material comprises pyrolytic graphite, graphitized polymer, or graphite foil made from compressed high purity exfoliated mineral graphite.

Aspect 22: An apparatus comprising:

at least one electrode element having a skin-facing surface;

a layer of anisotropic material having a skin-facing surface and an opposing outwardly facing surface;

a first layer of conductive adhesive or conductive gel/hydrogel positioned between the skin-facing surface of the at least one electrode element and the outwardly facing surface of the layer of anisotropic material; and a skin contact layer comprising a biocompatible conductive adhesive or conductive gel/hydrogel, wherein the skin contact layer is disposed on a skin-facing side of the layer of anisotropic material, wherein the first layer of conductive adhesive or conductive gel/hydrogel is configured to facilitate electrical contact between the skin-facing surface of the at least one electrode element and the outwardly facing surface of the layer of anisotropic material, wherein a plurality of openings extend through the layer of anisotropic material from the skin-facing surface to the outwardly facing surface.

Aspect 23: The apparatus of aspect 22, further comprising a second plurality of openings that extend through the first layer of conductive adhesive or conductive gel/hydrogel, and a third plurality of openings that extend through the skin contact layer, wherein the openings of the second plurality of openings and the openings of the third plurality of openings are coaxially aligned with respective openings of the plurality of openings of the layer of anisotropic material.

Aspect 24: The apparatus of any one of aspects 22-23, wherein the layer of anisotropic material comprises pyrolytic graphite, graphitized polymer, or graphite foil made from compressed high purity exfoliated mineral graphite.

Aspect 25: A method comprising:

applying an electrical field using the at least one electrode element of the apparatus of any one of aspects 22-24.

Aspect 26: A method comprising:

forming a plurality of openings that extend through a layer of anisotropic material of an apparatus, the apparatus comprising:

a first layer of conductive adhesive or conductive gel/hydrogel;

a skin contact layer comprising a biocompatible conductive adhesive or conductive gel/hydrogel; and the layer of anisotropic material, wherein the anisotropic material is disposed between the first layer of conductive adhesive or conductive gel/hydrogel and the skin contact layer.

Aspect 27: The method of aspect 26, further comprising forming a second plurality of openings that extend through the first layer of conductive adhesive or conductive gel/hydrogel, and a third plurality of openings that extend through the skin contact layer, wherein the openings of the second plurality of openings and the openings of the third plurality of openings are coaxially aligned with respective openings of the plurality of openings that extend through the layer of anisotropic material.

Aspect 28: The method of any one of aspects 25-27, wherein the layer of anisotropic material comprises pyrolytic graphite, graphitized polymer, or graphite foil made from compressed high purity exfoliated mineral graphite.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An apparatus comprising:
at least one electrode element having a skin-facing surface;
a layer of anisotropic material having a skin-facing surface and an opposing outwardly facing surface;
a first layer of conductive adhesive positioned between the skin-facing surface of the at least one electrode element and the outwardly facing surface of the layer of anisotropic material;
a skin contact layer comprising a biocompatible conductive adhesive, wherein the skin contact layer is disposed on a skin-facing side of the layer of anisotropic material; and
a circuit board, wherein the at least one electrode element is coupled to or a component of the circuit board,
wherein the first layer of conductive adhesive is configured to facilitate electrical contact between the skin-facing surface of the at least one electrode element and the outwardly facing surface of the layer of anisotropic material,
wherein a plurality of openings extend through the layer of anisotropic material from the skin-facing surface to the outwardly facing surface, and
wherein the circuit board has an outer perimeter having an outer perimeter shape, wherein the outer perimeter shape is superimposable on the layer of anisotropic material, and wherein all of the plurality of openings through the layer of anisotropic material are positioned outside of the outer perimeter shape.

2. The apparatus of claim 1, further comprising a second plurality of openings that extend through the first layer of conductive adhesive, and a third plurality of openings that extend through the skin contact layer, wherein the openings of the second plurality of openings and the openings of the third plurality of openings are coaxially aligned with respective openings of the plurality of openings of the layer of anisotropic material.

3. The apparatus of claim 1, wherein at least a first electrode element of the at least one electrode element is positioned within the outer perimeter of the circuit board.

4. The apparatus of claim 1, further comprising an absorbent or wicking material that overlies at least a portion of an outwardly facing surface of the first layer of conductive adhesive.

5. The apparatus of claim 4, wherein the absorbent or wicking material comprises a woven material or a superabsorbent material.

6. The apparatus of claim 5, wherein the superabsorbent material comprises cross-linked poly acrylic acid and/or copolymers thereof.

7. The apparatus of claim 1, further comprising at least one dielectric element, wherein a respective dielectric element of the at least one dielectric element is coupled to each electrode element of the at least one electrode element.

8. The apparatus of claim 1, wherein the first layer of conductive adhesive comprises:
a dielectric material; and
conductive particles dispersed within the dielectric material.

9. The apparatus of claim 1, wherein the anisotropic material comprises graphite.

10. The apparatus of claim 1, wherein the anisotropic material comprises pyrolytic graphite, graphitized polymer, or graphite foil made from compressed high purity exfoliated mineral graphite.

11. A method comprising:
forming a plurality of openings that extend through a layer of anisotropic material of an apparatus, the apparatus comprising:
a first layer of conductive adhesive;
a circuit board that is coupled to the first layer of conductive adhesive;
a skin contact layer comprising a biocompatible conductive adhesive; and
the layer of anisotropic material, wherein the anisotropic material is disposed between the first layer of conductive adhesive and the skin contact layer, wherein the circuit board has an outer perimeter, wherein the first layer of conductive adhesive is disposed between the circuit board and the layer of anisotropic material, and wherein forming the plurality of openings in the layer of anisotropic material comprises forming the plurality of openings only outside of the perimeter of the circuit board.

12. The method of claim 11, further comprising forming a second plurality of openings that extend through the first layer of conductive adhesive, and a third plurality of openings that extend through the skin contact layer, wherein the openings of the second plurality of openings and the openings of the third plurality of openings are coaxially aligned with respective openings of the plurality of openings that extend through the layer of anisotropic material.

13. The method of claim 11, further comprising coupling a circuit board to the first layer of conductive adhesive after forming the plurality of openings in the layer of anisotropic material.

14. The method of claim 11, wherein forming the plurality of openings in the layer of anisotropic material comprises forming the plurality of openings with a roller having protrusions configured to provide such openings.

15. The method of claim 11, wherein the layer of anisotropic material comprises pyrolytic graphite, graphitized polymer, or graphite foil made from compressed high purity exfoliated mineral graphite.

16. The apparatus of claim 1, wherein the skin contact layer is disposed on the skin-facing surface of the layer of anisotropic material.

17. An apparatus comprising:
a circuit board;

at least one electrode element having a skin-facing sur-
face, wherein the at least one electrode element is
coupled to or a component of the circuit board;

a layer of anisotropic material having a skin-facing sur-
face and an opposing outwardly facing surface;

a first layer of conductive adhesive positioned between
the skin-facing surface of the at least one electrode
element and the outwardly facing surface of the layer of
anisotropic material; and a skin contact layer comprising a biocompatible conduc-
tive adhesive, wherein the skin contact layer is dis-
posed on a skin-facing side of the layer of anisotropic
material, wherein the first layer of conductive adhesive is config-
ured to facilitate electrical contact between the skin-
facing surface of the at least one electrode element and
the outwardly facing surface of the layer of anisotropic
material, wherein a plurality of openings extend through the layer
of anisotropic material from the skin-facing surface to
the outwardly facing surface, a second plurality of openings extend through the first layer of conductive
adhesive, and a third plurality of openings extend
through the skin contact layer, and wherein the open-
ings of the second plurality of openings and the open-
ings of the third plurality of openings are coaxially
aligned with respective openings of the plurality of
openings of the layer of anisotropic material, and wherein all of the plurality of openings extend through all
layers of the apparatus except the circuit board.

18. The apparatus of claim 17, wherein the circuit board
has an outer perimeter, and wherein at least one electrode
element of the at least one electrode element is positioned
within the outer perimeter of the circuit board.

19. The apparatus of claim 17, wherein the anisotropic
material comprises graphite.

20. The apparatus of claim 17, wherein the anisotropic
material comprises pyrolytic graphite, graphitized polymer,
or graphite foil made from compressed high purity exfoli-
ated mineral graphite.

* * * * *